(12) United States Patent
Juturu et al.

(10) Patent No.: US 7,576,132 B2
(45) Date of Patent: Aug. 18, 2009

(54) ARGININE SILICATE INOSITOL COMPLEX AND USE THEREOF

(75) Inventors: Vijaya Juturu, Dobbs Ferry, NY (US); James R. Komorowski, Trumbull, CT (US)

(73) Assignee: Nutrition 21, Inc., Purchase, NY (US)

( * ) Notice: Subject to any disclaimer, the term of this patent is extended or adjusted under 35 U.S.C. 154(b) by 864 days.

(21) Appl. No.: 11/146,620

(22) Filed: Jun. 6, 2005

(65) Prior Publication Data
US 2005/0234019 A1  Oct. 20, 2005

Related U.S. Application Data

(62) Division of application No. 10/646,075, filed on Aug. 22, 2003, now abandoned.

(60) Provisional application No. 60/405,749, filed on Aug. 22, 2002.

(51) Int. Cl.
*A61K 31/70*  (2006.01)
*A61K 31/195*  (2006.01)

(52) U.S. Cl. ........................ 514/565; 514/23

(58) Field of Classification Search ............... 514/23, 514/565
See application file for complete search history.

(56) References Cited

U.S. PATENT DOCUMENTS

| | | | |
|---|---|---|---|
| 3,337,403 | A | 8/1967 | Zentner |
| 4,297,349 | A | 10/1981 | Barcza |
| 4,385,052 | A | 5/1983 | Zackheim et al. |
| 4,573,996 | A | 3/1986 | Kwiatek et al. |
| 4,597,961 | A | 7/1986 | Etscorn |
| 4,839,174 | A | 6/1989 | Baker et al. |
| 4,908,213 | A | 3/1990 | Govil et al. |
| 4,943,435 | A | 7/1990 | Baker et al. |
| 5,217,997 | A | 6/1993 | Levere et al. |
| 5,250,569 | A | 10/1993 | Godfrey |
| 5,284,657 | A | 2/1994 | Lu et al. |
| 5,288,497 | A | 2/1994 | Stanley et al. |
| 5,622,980 | A | 4/1997 | Caldwell et al. |
| 5,662,920 | A | 9/1997 | Santus |
| 5,707,970 | A | 1/1998 | McCarty |
| 5,716,610 | A | 2/1998 | Jack et al. |
| 5,763,392 | A | 6/1998 | Hansen et al. |
| 5,763,496 | A | 6/1998 | Holland |
| 5,804,203 | A | 9/1998 | Hahn et al. |
| 6,066,659 | A | 5/2000 | Speck |
| 6,123,936 | A | 9/2000 | Platz et al. |
| 6,132,394 | A | 10/2000 | Lankinen |
| 6,156,735 | A | 12/2000 | McCarty |
| 6,182,655 | B1 | 2/2001 | Keller et al. |
| 6,298,847 | B1 | 10/2001 | Datta et al. |
| 6,344,444 | B1 | 2/2002 | McCarty |
| 6,387,394 | B1 | 5/2002 | Baichwal et al. |
| 6,418,926 | B1 | 7/2002 | Chawla |
| 6,803,456 | B1 | 10/2004 | Kuhlmann |
| 2002/0068365 | A1 | 6/2002 | Kuhrts |

FOREIGN PATENT DOCUMENTS

| | | |
|---|---|---|
| FR | 2745498 | 9/1997 |
| FR | 2610522 | 8/1998 |
| WO | WO 98/34647 | 8/1998 |
| WO | 00/45651 A | 8/2000 |
| WO | 02/28379 A | 4/2002 |

OTHER PUBLICATIONS

Bassler, T.J. (1978) Hard water, food fiber, and silicon. British Medical Journal. 1:919.
Bonnefont-Rkousselot (2002) Glucose and reactive oxygen species. Curr. Opin. Clin. Nutr. Metab. Care 5:561-568.
Calver, et al. (1992) Effect of local intra-arterial $N^G$-monomethyl-L-arginine in patients with hypertension: the nitric oxide dilator mechanism appears abnormal. J. of Hypertension. 10:1025-1031.
Carlisle, E.M. (1972) Silicon: An essential element for the chick. Science 178:619-621.
Carlisle, E.M. (1976) In vivo requirement for silicon in articular cartilage and connective tissue formation in the chick. J. Nutr. 106:478-484.
Carlisle, et al. (1978) A requirement for silicon for bone growth in culture. Fed. Proc. 37:404.
Carlisle, et al. (1980) A silicon requirement for normal growth of cartilage in culture. Fed. Proc. 39:787.
Carlisle, E.M. (1980) Biochemical and morphological change associated with long bone abnormalities in silicon deficiency. J. Nutr. 110:1046-1055.
Chen, P.Y., et al. (1991) L-arginine abrogates salt-sensitive hypertension in dahl/rapp rats. J. Clin. Invest. 88:1559-1567.
Clarkson, et al. (1996) Oral L-arginine improves endothelium-dependent dilation in hypercholesterolemic young adults. J. Clin. Invest. 97(8):1989-1994.
Clowes, et al. (1977) Suppression by heparin of smooth muscle cell proliferation in injured arteries. Nature. 265:625-626.
Cooke, et al. (1994) Is NO an endogenous antiatherogenic molecule. Arteriosclerosis and Thrombosis. 14(5):653-655.
Creager, et al. (1992) L-arginine improves endothelium-dependent vasodilation in hypercholesterolemic humans. J. Clin. Invest. 90:1248-1253.

(Continued)

*Primary Examiner*—Raymond J Henley, III
(74) *Attorney, Agent, or Firm*—Knobbe Martens Olson & Bear LLP

(57) ABSTRACT

A method for preventing and treating a variety of disease states and disorders is provided, comprising the administration of an arginine silicate inositol complex to an individual in the presence of medical therapy or absence of medical therapy. Examples of said disease states and disorders include bone and cartilage disorders and cardiovascular disease and its associated micro and macro vascular complications including infections and inflammation of all these diseases in combination or without. Advantageously, the amount of arginine silicate inositol complex administered per day is between about 2 mg/Kg body weight to 2,500 mg/Kg body weight or from a low dose to a higher dose to observe normal metabolic functions and healthy and the delivery is parenteral, oral or intravenous or topical by solid or liquid or both.

15 Claims, 1 Drawing Sheet

OTHER PUBLICATIONS

Curtis, et al. (1997) Nitric oxide supplementation or synthesis block—which is the better approach to treatment of heart disease?, Trends in Pharmacological Sciences. 18(7):239-244.

Drexler, et al.(1991) Correction of endothelial dysfunction in coronary microcirculation of hypercholesterolaemic patients by L-arginine. Lancet. 338:1546-1550.

Edelman, et al. (1990) Effect of controlled adventitial heparin delivery on smooth muscle cell proliferation following endothelial injury. Proc. Natl. Acad. Sci. USA. 87:3773-3777.

Eisinger et al. (1993) Effects of silicon, fluoride, etidronate and magnesium on bone mineral density: a retrospective study. Magnisium Research. 6(3):247-249.

Garson, et al. (1971) Organosilicon entities as prophylactic and therapeutic agents. J. of Pharmaceutical Sciences. 60(8):1113-1127.

Guyton, et al. (1980) Inhibition of rat aterial smooth muscle cell proliferation by heparin. Circ. Res. 46:625-634.

Harrison's Principles of Internal Medicine, 13$^{th}$ edition, vol. 2, Isselbacher et al. (eds.), published 1994 by McGraw-Hill in 1994, p. 1321.

Hott et al. (1993) Short-term effects of organic silicon on trabecular bone in mature ovariectomized rats. Calcif. Tissue Int. 53:174-179.

Laurant, et al. (1995) Dietary L-arginine attenuates blood pressure in mineralocorticoid-salt hypertensive rats. Clin. and Exper. Hypertension 17(7):1009-1024.

Loeper, et al. (1979) The antiatheromatous action of silicon. Atherosclerosis 33:397-408.

Loeper, et al. (1978) The physiological role of the silicon and its antiatheromatous action, in biochemistry of silicon and related problems. Bendz G. et al. Eds. Plenum Press, NY 281-296.

Luscher, T.F. (1991) Endothelium-derived nitric oxide: The endogenous nitrovasodilator in the human cardiovascular system. Eur. Heart J., 12(Suppl. E):2-11.

Maulik, et al. (1995) Nitric oxide signaling in ischemic heart. Cardiovasc. Res. 30(4):593-601.

McPherson et al. (2002) Superoxide activates constitutive nitric oxide synthase in a brain particulate fraction. Biochemical and Biophysical Research Communications. 296:413-418.

Moncada, et al. (1993) The L-arginine-nitric oxide pathway. The New. Engl. J. of Med. 329(27):2002-2012.

Parr, R.M. (1980) Silicon, wine, and the heart. Lancet p. 1087.

Rubanyi, M.D., Ph.D. (1991) endothelium-derived vasoactive factors in health and disease, in cardiovascular significance of endothelium-derived vasoactive factors. Rubanyi, G.M., ed., Futura Publishing Company, Inc., NY xi-xix.

Schwarz,et al. (1972) Growth-promoting effects of silicon in rats. Nature. 239:333-334.

Schwarz, K., Silicon (1977) Fiber, and atherosclerosis. Lancet. 454-457.

Schwarz,et al. (1977) Inverse relation of silicon in drinking water and atherosclerosis in finland. Lancet 538-539.

Schwarz, K. (1978) Significance and functions of silicon in warm-blooded animals, in biochemistry of silicon and related problems. Bendz, G. et al., Eds., Plenum Press, NY 207-230.

Svehla, G. (1979) Reaction of silicates. Vogels Textbook of Macro and Semimicro Qualitative Inorganic Analysis 5$^{th}$ Edition, Longman, London pp. 350-353.

Tsao, et al. (1994) Enhanced endothelial adhesiveness in hypercholesterolemia is attenuated by L-arginine. Circulation 89(5):2176-2182.

Wang et al. (1999) Effects of nitric oxide synthase inhibitors on systemic hypotension, cytokines and inducible nitric oxide synthase expression and lung injury following indotoxin administration in rats. J. Biomed. Sci. 6:28-35.

Miller, et al. "Practical Clinical Application of Biochemical Markers of Bone Turnover." Journal of Clinical Densitometry. 2(3):323-342 (1999).

Partial European Search Report for European Application No. 03793307.4, dated Aug. 2, 2007.

Calles-Escandon et al. "Diabetes and endothelial dysfunction: A clinical perspective." Endocrine Reviews. 22(1):36-52 (2001).

Kelly et al. "Insulin resistance: lifestyle and nutritional interventions." Alternative Medicine Review. 5 (2):109-132 (2000).

Van Lente. "Markers of inflammation as predictors in cardiovascular disease." Clinica Chimica Acta. 293:31-52 (2000).

Proctor et al. "A novel complex of arginine-silicate improved micro and macrovascular function and inhibits glomerular sclerosis in insulin-resistant JCR:LA-cp rats." Diabetologia. 48(9):1925-1932 (2005).

Proctor et al. "Metabolic effects of a novel silicate inositol complex of the nitric oxide precursor arginine in the obese insulin-resistant JCR:LA-cp rat." Metabolism. 56(10):1318-1325 (2007).

Supplementary European Search Report for European Application No. EP 03793307.4 dated Dec. 4, 2008.

ARGININE SILICATE INOSITOL COMPLEX AND USE THEREOF

RELATED APPLICATIONS

This application is a divisional of and claims priority to U.S. patent application Ser. No. 10/646,075, filed Aug. 22, 2003, now abandoned, which claims priority to U.S. Patent Application No. 60/405,749, filed Aug. 22, 2002, the disclosure of which is hereby incorporated in its entirety. This application is related to U.S. Pat. No. 5,707,970 filed Feb. 12, 1997, U.S. Pat. No. 6,156,735, filed Dec. 13, 1999, and U.S. Pat. No. 6,344,444, filed Dec. 5, 2000.

BACKGROUND OF THE INVENTION

1. Field of the Invention

The present invention relates to an arginine silicate inositol complex and its use in the prevention and treatment of a variety of disease states and disorders.

2. Description of the Related Art

Until recently, infectious disease had been the greatest threat to public health and welfare in the United States and other developed societies. However, the advent of modern vaccines and antibiotics, along with increasing longevity, changing dietary habits, and a lack of physical activity, have raised the importance of degenerative disorders as a threat to health. Examples of such chronic diseases include osteoporosis, arthritis, type II diabetes, and cardiovascular disease. A common factor in the development of many of these disorders is "metabolic syndrome" or "syndrome X", which is characterized by increased glucose intolerance and insulin resistance and results in hyperinsulinemia, obesity, dyslipidemia, hypertension, disturbances in hormone function and immune function, and atherosclerosis.

Measures to prevent and oftentimes to treat these disorders usually begin with lifestyle and dietary changes. However, these interventions meet with a varying degree of success, due in part to the rigid requirements of some prescribed regimens. In light of this, as well as the increasing incidence of obesity in all age groups, there is great interest in pharmaceutical and nutraceutical research to find drugs and supplements to prevent and treat these disorders.

An example of such a disorder is atherosclerosis, which is a complex and chronic disease involving the gradual accumulation of lipids, collagen, elastic fibers and proteoglycans in the arterial wall. Current methods of managing atherosclerosis include a low-fat diet, exercise and various cholesterol-lowering drugs. Although these methods can significantly retard the progression of atherosclerosis, they are not entirely satisfactory.

Heparin sulfate proteoglycans (HSPGs) produced by vascular endothelium are believed to retard the migration, multiplication and phenotypic transition of vascular smooth muscle cells, events which play a central role in the atherogenic process, and to maintain an anticoagulant luminal surface by binding and activating antithrombin III (Clowes et al., Nature, 265:625-626, 1977; Guyton et al., Circ. Res., 46:625-634, 1980; Edelman et al., Proc. Natl. Acad. Sci. U.S.A., 87:3773-3777, 1990).

Various silicon compounds administered orally or parenterally have been demonstrated to inhibit cholesterol-induced intimal hyperplasia (atherosclerosis) in rabbits (Loeper et al., Athersclerosis, 33:397-408, 1979; Loeper et al., in Biochemistry of Silicon and Related Problems, Plenum Press, New York, 1978, pp. 281-296; Garson et al., J. Pharm. Sci., 60:1113-1127, 1971). The injection or ingestion of nutritionally available silicon compounds (i.e. monomethyltrisilanol, lysine silicate, sodium silicate) prevented the characteristic intimal thickening and fragmentation of arterial elastic fibers observed in atherosclerosis. Additionally, several epidemiological studies report that increased dietary intakes of silicon are associated with a reduced risk of coronary heart disease in humans (Schwarz et al., Lancet, i:454-457, 1977; Schwarz et al., Lancet, i:538-539, 1977; Bassler, Brit. Med. J., 1:919, 1978; Parr, Lancet, i:1087, 1980).

Evidence suggests that silicon intake can also affect bone and joint health. Studies in growing young rats and chicks show that severe dietary silicon deficiency results in abnormal bone and joint structures, apparently due to subnormal production of collagen and mucopolysaccharides (Carlisle, J. Nutr. 106:478-484, 1976; Carlisle, J. Nutr. 110:1046-1055, 1980). Silicon promotes the synthesis of collagen and mucopolysaccharides in vitro (Carlisle et al., Fed. Proc. 37:404, 1978; Carlisle et al., Fed. Proc. 39:787, 1980). The biochemical method by which silicon achieves this effect are unknown. Silicone has been shown to enhance bone mineral density. When an organosilicon compound (monomethyltrisilanol) was administered to postmenopausal women by injection at a dose of 50 mg twice weekly, femoral density increased significantly by an average of 4.7% over 14 months of administration (Eisinger et al., Magnesium Res. 6:247-249, 1993). In ovariectomized rats, oral orthosilicic acid slowed bone turnover and increased the bone formation rate (Hott et al., Calcif. Tissue Int. 53:174-179, 1993).

Bone and cartilage are dynamic tissues in both juvenile and adult animals. In bone, osteoclasts solubilize the hydroxyapatite bone matrix and degrade collagen, whereas osteoblasts concurrently rebuild bone through collagen synthesis and hydroxyapatite deposition. Analogously, chondrocytes in cartilage simultaneously degrade the collagen and proteoglycan matrix and resynthesize it. The impact of silicone on bone and cartilage formation in adult animal is essentially unknown. However, it is highly unlikely that the role of silicon in bone and cartilage metabolism is limited to juvenile animals.

The nutritional role of silicon is to support adequate synthesis of mucopolysaccharides, proteoglycans and collagen (Schwarz et al., Nature, 239:333-334, 1972; Carlisle, Science, 178:619-621, 1972; Carlisle, J. Nutr., 106:478-484, 1976; Schwarz, in Biochemistry of Silicon and Related Problems, Plenum Press, New York, 1978, pp. 207-230). Optimal silicon nutrition may promote production of protective HSPGs by endothelial cells.

Arginine, an essential amino acid, is the biosynthetic precursor for the nitric oxide (NO) produced by vascular endothelium (Moncada, New Engl. J. Med., 329:2002-2012, 1993). NO exerts vasodilatory, antiatherosclerotic, antithrombotic and antioxidant effects, and deficient endothelial production of NO may play a prominent pathogenic role in atherosclerosis, hypertension and diabetes (Calver et al., J. Hypertension, 10:1025-1031, 1992; Cooke et al., Arterioscler. Thromb., 14:653-655, 1994; Rubanyi, in: Cardiovascular Significance of Endothelium-Derived Vasoactive Factors, Futura Publishing Co, Inc., New York, 1991, pp. xi-xix; Bonnefont-Rousselot, Curr. Opin. Clin. Nutr. Metab. Care, 5:561-568, 2002; McPherson et al., Biochem. Biophys. Res. Comm., 296:413, 2002). In some though not all clinical studies, parenteral or oral administration of arginine has enhanced vascular NO synthesis (Drexler et al., Lancet, 338:1546-1550, 1991). In animal models of hypertension, arginine supplementation has moderated the increase in blood pressure (Chen et al., J. Clin. Invest., 88:1559-1567, 1991; Laurant et al., Clin. Exp. Hyperten., 17:1009-1024, 1995). Thus, under at least some circumstances, arginine availability can be rate-limiting for NO production. A recently published clinical study indicates that oral arginine can enhance endothelium-dependent relaxation in hypercholesterolemic young people (Creager et al., *J. Clin. Invest.*, 90:1248-1253, 1992; Clarkson et al., *J. Clin. Invest.*, 97:1989-1994, 1996) which is indicative of increased efficiency of vascular NO production.

Also related to metabolic syndrome is a condition affecting women called Polycystic Ovary Syndrome (PCOS) or Stein-Leventhal Syndrome. This syndrome affects an estimated 5% to 10% of women. The condition is characterized by 1) irregular or absent menses, 2) numerous cysts on the ovaries, 3) high blood pressure, 4) acne, 5) elevated insulin levels, insulin resistance, or type II diabetes, 6) infertility, 7) excess hair on the face or body, 8) male-pattern baldness, 9) abdominal obesity, and 10) abnormal lipid profiles.

The hallmark features of PCOS are obesity, insulin resistance, abnormal lipid profile, excessive hair growth, anovulation, and infertility. Studies with insulin sensitizers ("glitazones") have demonstrated some beneficial effects on this patient population with respect to these characteristics. Recently, the safety of glitazones has been challenged given the increased frequency of liver toxicity.

There is a constant need for therapeutic/prophylactic agents capable of preventing or retarding the progression of cardiovascular diseases and disorders, promoting the formation of bone and cartilage, and preventing and treating diseases and disorders related to metabolic syndrome, including diabetes. The present invention addresses these needs.

SUMMARY OF THE INVENTION

Figure 1:
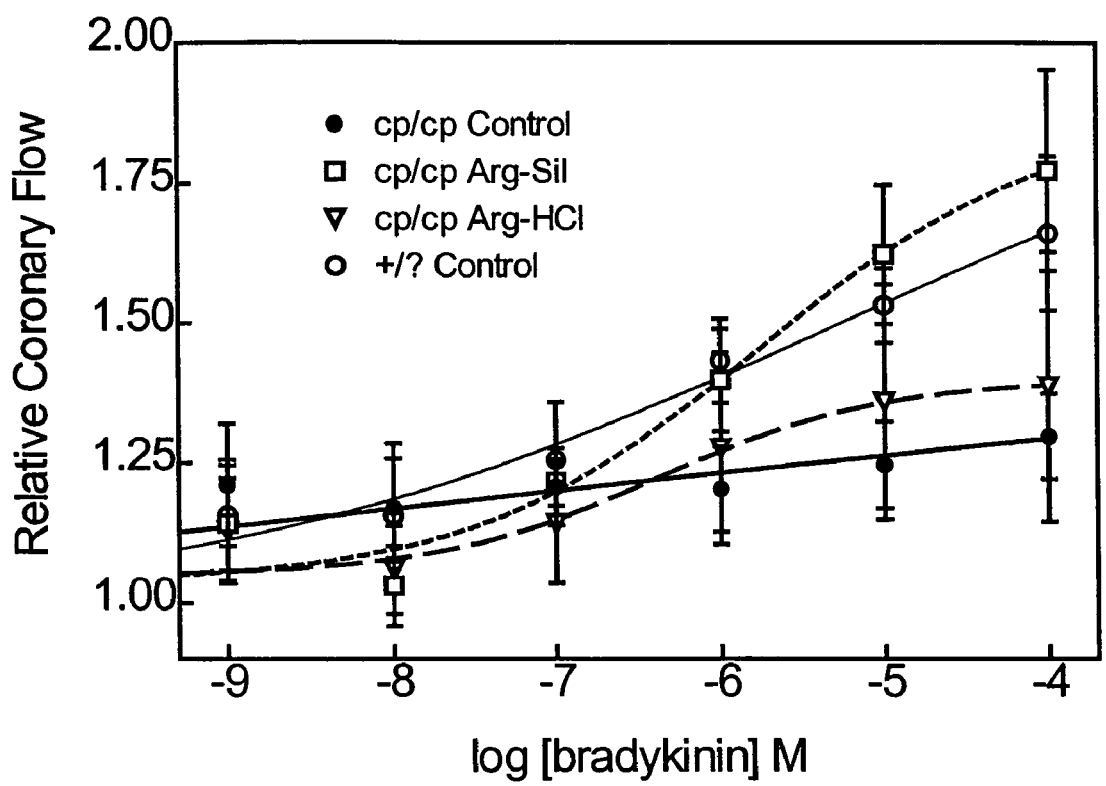
FIG. 1 is a graph of data from Example 4, showing relative coronary flow versus log bradykinin concentration. Samples were taken from Langendorf-perfused hearts of JCR:LA-cp rats, control and arginine-treated. Values are mean±SEM, 10 rats in each group.

The disclosed invention is directed to methods of ameliorating the biochemical markers of disease states and disorders and/or the treatment or prevention of the disease states or disorders. The methods include administering to a subject an effective dose of a composition containing an arginine silicate inositol complex.

The present invention provides a method for ameliorating the symptoms associated with a bone or cartilage disorder in an individual in need thereof, comprising administering to the individual an effective amount of the arginine silicate inositol complex. In one aspect of the invention, the bone disorder is osteoporosis, osteogenesis imperfecta, or bone fractures. In another aspect of the invention, the cartilage disorder is osteoarthritis, inflammatory arthritis, a torn tendon or a torn ligament. In another aspect of the invention, the bone and cartilage disease or disorders associated with chronic diseases such as diabetes cardiovascular disease, obesity etc Preferably, the administration is parenteral or oral. Advantageously, the effective amount is between about 2 mg and about 2,500 mg. More advantageously, the effective amount is between about 500 mg and about 1,000 mg. For the average 70 kg man, this equals a dosage of between about 3.6 and 14 mg/kg (250-2,500 mg) and between about 7.1 mg/kg and 14 mg/kg (500 mg-1,000 mg), respectively.

The present invention also provides a method of increasing the levels of type I collagen in an individual, preferably a mammal, comprising the step of administering to the individual an effective amount of an arginine-silicate-inositol complex. Preferably, the administering step is parenteral or oral. Advantageously, the effective amount is between about 250 mg and about 2,500 mg; more advantageously, the effective amount is between about 500 mg and about 1,000 mg.

A further aspect of the invention is a method of increasing bone length in an individual, preferably a mammal, comprising the step of administering to the individual an effective amount of an arginine-silicate-inositol complex. Preferably, the administering step is parenteral or oral.

The present invention also provides a method of improving and reducing the infections and infectitious diseases and decreases the inflammatory markers associated with cardiovascular disease and bone and joint health disease or disorders in an individual, preferably a mammal, and infections associated with cardiovascaular diseases, bone and joint health disorders and associated complications comprising the step of administering to the individual an effective amount of an arginine-silicate-inositol complex. Preferably, the administering step is parenteral or oral. Advantageously, the effective amount is between about 2 mg and about 2,500 mg.

The present invention also provides a method of reducing the risk of damage due to inflammatory diseases and infections of the brain, heart, lungs, liver, kidneys, skin and gastrointestinal tract. Such inflammatory diseases and infections includes bacterial, fungal and viral diseases, such as cysticercosis, bacterial meningitis, tuberculosis, sarcoidosis, complications of meningitis, herpes simplex virus infection, lyme disease, congenital infections, toxoplasmosis, cytomegalovirus (CMV) infection, rubella, human immunodeficiency virus (HIV) infection, Acquired Immunodeficiency Syndrome (AIDS)-related infections, encephalitis (including post-infection encephalitis and encephalitis caused by HIV or CMV), cryptococcosis and progressive multifocal leukoencephalopathy (PML). Other treatable disorders include, but are not limited to, arthritis, inflammatory skin conditions, transplant-related diseases, inflammatory bowel diseases, cancer, allergies, cardiovascular diseases, rheumatoid arthritis, asthma, chronic obstructive pulmonary disease and endocrine system-related diseases.

Inflammation is one part of the body's response to injury, infection or molecules perceived by the immune system as foreign. Clinically, inflammation is characterized by pain, redness, heat, swelling and altered function of affected tissue. Although the ability to mount an inflammatory response is essential for survival, the ability to control inflammation is also necessary for health. Absent such control, excessive or uncontrolled inflammation results in a vast array of diseases that includes the highly prevalent conditions of allergy, including allergic rhinitis/sinusitis, skin allergies (urticaria/hives, angioedema, atopic dermatitis), food allergies, drug allergies, insect allergies, and rare allergic disorders such as mastocytosis; asthma; arthritis, including osteoarthritis, rheumatoid arthritis, and spondyloarthropathies; autoimmune conditions, including systemic lupus erythematosus, dermatomyositis, polymyositis, inflammatory neuropathies (Guillain Barré, inflammatory polyneuropathies), vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arthritis.

The present invention also provides a method of decreasing cross linked N-telpeptides (NTx), reducing inflammatory markers of arthritis and osteoporosis, improving the markers of bone formation (serum osteocalcin, alkaline phosphatase) and bone resorption markers (hydroxy proline; total, peptide bound and free pyridinium cross-links), comprising the step of administering to the individual an effective amount of an arginine-silicate-inositol complex. Preferably, the administering step is parenteral or oral or intravenous. Advantageously, the effective amount is between about 2 mg and about 2,500 mg.

The present invention also provides a method for the prevention of bone and cartilage disease or disorders, with or without any chronic disease present, preferably affecting normal bone and cartilage functions, comprising the step of administering to an individual an effective amount of an arginine-silicate-inositol complex. Preferably, the administering step is parenteral or oral or intravenous. Advantageously, the effective amount is between about 2 mg and about 2,500 mg.

A further aspect of the invention is a method of increasing bone length in an individual, preferably a mammal, comprising the step of administering to the individual an effective amount of an arginine-silicate-inositol complex. Preferably, the administering step is parenteral, oral or intravenous. Another aspect of the invention is a method for the revention of bone mass loss, improvement of bone mineral content and maintenance of healthy bone and cartilage comprising the step of administering to an individual an effective amount of an arginine-silicate-inositol complex. Preferably, the administering step is parenteral, oral or intravenous. Advantageously, the effective amount is between about 2 mg and about 2,500 mg.

Another aspect of the present invention is a method of treating the weakening of bone due to a reduction in mechanical stress comprising the step of administering to said individual an effective amount of an arginine-silicate-inositol complex. Preferably, the cause of the reduction of mechanical stress is exposure to weightlessness or immoblization in an individual. In one aspect of the invention, the administering of the arginine silicate inositol complex for the treatment of the weakening of bone due to a reduction in mechanical stress is done prophylatically. Advantageously, the administering step is parenteral or oral. An additional aspect of the invention is a method of treating bone fractures, cartilage injury, brittleness of the bones and maintaining structural integrity of bone and cartilage comprising the step of administering to said individual as effective amount of an arginine-silicate inositol complex.

Still another aspect of the invention is a method of treating coronary vascular disease and diseases secondary to coronary vascular disease in an individual, preferably a mammal, more preferably a human, comprising the step of administering to the individual an effective amount of an arginine-silicate-inositol complex. An additional aspect of the invention is a method of improving the coronary vascular health of an individual, preferably a mammal, more preferably a human, comprising the step of administering to the individual an effective amount of an arginine-silicate-inositol complex. Additional aspects of the invention are methods of restoring normal cardiovascular function, maintaining cardiovascular integrity, preventing ischemic changes, preventing myocardial infarction, improving vascular relaxation, reducing vascular contractility and normalizing vascular function comprising the step of administering to the individual an effective amount of an arginine-silicate-inositol complex. Methods of treating pre existing conditions of cardiovascular disease, complications and associated diseases, and of treating metabolic syndrome, comprising the step of administering to the individual an effective amount of an arginine-silicate-inositol complex, are also aspects of the invention.

An additional aspect is a method of treating diseases secondary to coronary vascular disease, preferably nephroscle-rosis, abnormal liver lipid concentrations, microvascular complications, or macrovascular complications, comprising the step of administering to the individual an effective amount of an arginine-silicate-inositol complex.

Another embodiment of the invention is a method for increasing estrogen levels, preventing hormonal imbalance and maintaining normal hormonal function in an individual, preferably a mammal, more preferably a human, comprising the step of administering to the individual an effective amount of an arginine-silicate-inositol complex.

Another embodiment of the invention is a method of treating disorders caused by hormonal imbalance and restoring hormone level homeostasis and normal metabolic function in an individual, preferably a mammal, comprising the step of administering to the individual an effective amount of an arginine-silicate-inositol complex.

Yet another embodiment of the invention is a method of increasing nitric oxide production in an individual, preferably a mammal, more preferably a human, comprising the step of administering to the individual an effective amount of an arginine-silicate-inositol complex. In some embodiments, this complex is a fast release arginine-silicate-inositol complex, or extended release arginine silicate inositol complex and/or a slow release arginine silicate inositol complex.

Yet another embodiment of the invention is a method of controlled release of arginine silicate inositol complex that modulates the contributing risk factors of bone and joint health disease or disorders, as well as cardiovascular disease, associated disorders and complications. In some embodiments, the controlled release of arginine-silicate-inositol is in combination with medications for the treatment of bone and joint diseases and disorders, or for the treatment of cardiovascular disease, associated disorders and complications. In some embodiments, the controlled release of arginine-silicate-inositol is in combination with agents that lower the risk of bone, joint and/or cardiovascular diseases, disorders or complications.

Still another embodiment of the invention is a method for treating disorders caused by or exacerbated by reduced levels of nitric oxide, preferably pulmonary hypertension, renal disease, atherosclerosis, coronary heart disease, myocardial infarction, ischemia, stroke, hypertension, diabetes, hypercholesterolemia, hyperglycemia, heart failure, Fabry's disease, chronic obstructive pulmonary disease (COPD), inflammatory bowel disease, Crohn's disease, ulcerative colitis, perinatal asphyxia, meconium aspiration syndrome, Group B streptococcus sepsis, congenital diaphragmatic hernia, ischemic heart disease, hyperhomocysteinemia, multiple sclerosis, Takayasu's arteritis, autosomal dominant polycystic kidney disease, end-stage renal failure, cancer, or liver disease, by increasing concentrations of nitric oxide in an individual, preferably a mammal, more preferably a human, comprising the step of administering to the individual an effective amount of an arginine-silicate-inositol complex.

In another aspect of the present invention, a method of reducing the concentration of a marker for bone resorption in a clinical sample taken from an individual, preferably a mammal, more preferably a human, comprising the step of administering to the individual an effective amount of an arginine-silicate-inositol complex is provided. The marker for bone resorption may be pyridinoline cross-linking peptides, including C- and N-telopeptides, N-telopeptide cross-links (NTx), C-telopeptide cross links (CTx) and pyridinoline cross-linked carboxyterminal peptides (ICTP), total, peptide-bound and free pyridinoline, hydroxyproline, deoxypyridinoline, tartrate-resistant acid phosphatase or bone sialoprotein.

In still another aspect of the invention, a method for increasing the concentration of a marker for bone formation in a clinical sample from an individual, preferably a mammal, more preferably a human, comprising the step of administering to the individual an effective amount of an arginine-silicate-inositol complex is provided. The marker of bone formation may be osteocalcin, alkaline phosphatase or procollagen type I C-/N-extension peptides (PICP, PINP).

An additional aspect of the invention is a method of reducing markers of poor cardiovascular health, preferably urinary albumin concentration or vascular contractility, in an individual, preferably a mammal, more preferably a human, comprising the step of administering to the individual an effective amount of an arginine-silicate-inositol complex. Additional aspects of the invention include methods for improving bradykinin response, coronary blood flow, improving vascular health and reducing atherosclerotic plaques in an individual, preferably a mammal, more preferably a human, comprising the step of administering to the individual an effective amount of an arginine-silicate-inositol complex.

A further aspect of the invention is a method of improving markers of good cardiovascular health, preferably vascular relaxation, in an individual, preferably a mammal, comprising the step of administering to the individual an effective amount of an arginine-silicate-inositol complex.

DETAILED DESCRIPTION OF THE PREFERRED EMBODIMENTS

The present invention describes methods of using an arginine silicate inositol complex produced by combining arginine, a silicate salt and inositol, for the prevention and treatment of a wide variety of disorders and disease states. Although the product described herein contains arginine, silicate and inositol, it may be referred to in the specification as "arginine silicate."

Arginine silicate inositol is synthesized by reacting arginine (free base), potassium silicate and inositol as described in Example 1. The resulting complex is completely soluble and provides silicate in a bioavailable form, which will have an improved nutritional availability. Silicates are typically insoluble in aqueous solutions. However, the use of inositol in the synthesis of the arginine silicate-containing complex renders the complex soluble in aqueous solution. In contrast, arginine silicate synthesized in the absence of inositol is insoluble in aqueous solutions. This unexpected solubilization effect of inositol is therefore helpful to the use of the complex as a bioavailable source of arginine and silicate. Inositol facilitates solubilization of arginine silicate by increasing hydrogen bonding between arginine and silicic acid. Although other polyhydroxy compounds including, but not limited to, mannitol and sorbitol can also be used, inositol is preferred. The bioavailability of silicate was confirmed as described in Example 3. In a preferred embodiment, the combining molar ratio of arginine to silicate is about 1:1 and the ratio of inositol to arginine and silicate is about 1:3. Although potassium silicate was used as a reactant, the use of other silicate salts including sodium silicate and magnesium silicate, is also within the scope of the invention. The mixture resulting from the combination of inositol, silicate salt and arginine is a highly viscous suspension which is clarified by heating. In a preferred embodiment, the suspension is heated to between about 80° C. and about 100° C., more preferably about 95° C., until clarification is observed. At this time, heating and stirring is discontinued and gel formation is initiated. Crystallization of the arginine silicate complex occurs as gel formation progresses. The resulting crystal bulk is dispersed and mixed with an alcohol for about 30 min. to effect more complete crystallization and recovery of a purer product. Heavy metal content of the final product is less than 5 ppm which is considered undetectable. The level of iron is also very low (10 ppm). These findings indicate that the product is virtually free of such contaminants. Although the use of ethanol for crystallization of the arginine silicate complex is preferred, the use of other alcohols is also contemplated. Optionally, a second alcohol crystallization step may be performed. The final product, a complex containing arginine, silicate and inositol, is collected by filtration, washed and dried.

Arginine silicate inositol may be used both as a source of the essential amino acid arginine and as a source of silicate, both of which exert antiatherosclerotic effects. The oral administration of this compound delivers arginine and silicate to appropriate sites of action. Arginine silicate inositol is useful as a therapeutic or preventative agent for atherosclerosis and may also be given as a dietary supplement to maintain an antiatherogenic state. Thus, the administration of arginine silicate inositol has prophylactic as well as therapeutic applications. Arginine silicate inositol is highly soluble in water and provides good nutritional availability of both arginine and silicate. In addition to providing silicate, the arginine silicate inositol complex is also a good dietary supplement for the essential amino acid arginine.

Described herein as a single formulation of the three specified ingredients, it is also anticipated that any of the three ingredients could be administered separately of the other two. The use of any of the ingredients in any combination or sequence with the other two and the use of an amino acid other than arginine to form the complex is also contemplated by this invention.

The arginine silicate inositol complex of the invention promotes bone and cartilage formation in a mammal in need thereof, particularly in humans. Bioavailable nutritional silicon in the form of the arginine silicate inositol complex described herein also increases bone density and prevents bone demineralization. In one preferred embodiment, the complex is administered prophylactically to prevent bone demineralization and cartilage degradation. One preferred use of the complex is prevention and treatment of osteoporosis, which results from bone demineralization in postmenopausal women. The complex is used to prevent or treat any bone demineralization disorder, including osteoporosis and osteogenesis imperfecta. The arginine silicate inositol complex is also used as an adjunct in the treatment of bone fractures. For example, an individual with a bone fracture is treated by casting in combination with oral administration of the arginine silicate inositol complex of the invention to promote faster healing of the fracture. This lessens the time the individual must wear the cast in situations where a cast is applied. The arginine silicate inositol complex can also be used to treat "green stick" fractures in which no actual separation of the bone has occurred.

The arginine silicate inositol complex of the invention is useful for improving treatments for bone and cartilage diseases and disorders. The complex can be administered to an individual being treated for such a disorder, for an additional reduction in disease symptoms or a speedier recovery. For example, an individual receiving calcium supplements and a bisphosphonate drug (which decreases bone resorption) for the treatment of osteoporosis is given arginine silicate inositol to affect greater increases in bone density than would be seen with the calcium and bisphosphonate alone. In another example, an individual receiving physical therapy for joint damage is given arginine silicate inositol to assist in repair of collagen in the afflicted joint tissue.

As used in the above paragraph, the term "a mammal in need thereof" refers to a subject suffering from or displaying symptoms of a bone disorder or a cartilage disorder or a subject at risk for suffering from or displaying symptoms of a bone disorder or a cartilage disorder. As used here, the term "at risk" refers to subjects experiencing a condition for the group comprising menopause, andropause, hypogonadism, advanced age and, for human subjects, being at least 60 years of age.

Due to the cumbersome, expensive and invasive nature of bone histomorphometry, osteoporosis researchers have developed biochemical tests for the presence of peptides and proteins that correlate with bone turnover rates in patients. Using these tests to analyze serum or urine samples, researchers are able to detect increased or decreased rates of bone resorption and bone formation in patients. These tests can be used to detect and quantify changes in the musculo-skeletal system caused by a variety of different conditions and disease states.

In another preferred embodiment of the invention, the complex is administered to patients with elevated levels of markers of bone resorption. These markers of bone resorption include, but are not limited to, pyridinoline cross-linking peptides, including C- and N-telopeptides, N-telopeptide cross-links (NTx), C-telopeptide cross links (CTx) and pyridinoline cross-linked carboxyterminal peptides (ICTP), free pyridinoline, deoxypyridinoline, tartrate-resistant acid phosphatase and bone sialoprotein. Increased levels of these markers may indicate bone loss in a patient. For example, a patient with elevated levels of N-telopeptides, measured in a urine or serum sample, would be administered an arginine silicate inositol complex in order to reduce the measured levels of that and other markers of bone resorption in clinical samples from that patient.

Another preferred embodiment features the administration of an arginine silicate inositol complex to a patient with reduced levels of markers for bone formation. These markers of bone formation include, but are not limited to, osteocalcin, alkaline phosphatase and procollagen type I C-/N-extension peptides (PICP, PINP). Reduced levels of these markers may indicate bone loss in a patient. For example, a patient with reduced levels of serum osteocalcin would be administered an arginine silicate inositol complex in order to increase the measured levels of that and other bone formation markers in clinical samples from that patient.

In another embodiment, an arginine silicate inositol complex is administered to an individual with torn cartilage or tendons either alone, or after surgery to repair the damaged area. By promoting cartilage formation, the arginine silicate inositol complex lessens the recovery time after surgery.

In some embodiments, an arginine silicate inositol complex is administered to an individual with any one or a number of different diseases and/or disorders, including bone and cartilage diseases or disorders such as osteoporosis, osteoarthritis, chondrosarcomas, enchondromas, osteochondromas, Ollier's disease, multiple exostoses, Maffucci's syndrome, avascular necrosis, fibrous dysplasia, osteogenesis imperfecta, osteomyelitis, Paget's disease of the bone, hyperparathyroidism, cardiovascular disease (including cardiovascular disease associated with micro and macro vascular complications), stable angina, unstable angina, pulmonary stenosis, peripartum cardiomyopathy, mitral regurgitation (acute or chronic), ischemic cardiomyopathy, hypertrophic cardiomyopathy, idiopathic hypertrophy, heart tumor, heart attack, congenital heart disease, dilated cardiomyopathy, heart failure, endocarditis, cardiogenic shock, tricuspid regurgitation, alcoholic cardiomyopathy, aortic regurgitation, aortic stenosis, arrhymias, abnormal heart rates, EKG changes, stroke, hypertension, ischaemic heart disease, coronary artery disease, myocardial infarction, chronic heart failure, congestive heart failure, dilated cardiomyopathy, rheumatic heart disease, chronic obstructive pulmonary disease (COPD), complications due to coronary artery bypass graft (CABG), drug- or alcohol-induced changes in heart function, abnormal functioning of the heart valves, abnormal electrical rhythm of the heart, reduction in ejection fraction (including reductions caused by infection or toxin exposure), surgical treatments, nutritional deficiencies, over nutrition, under nutrition, increasing levels of inflammatory markers, increasing inflammation due to infections and immune system dysfunction.

The host response to infection or injury initiates a cascade of events involving recruitment of leukocytes and the release of multiple inflammatory mediators. The endothelial cell layer displays the features of a distributed organ and has a variety of biological functions, such as maintaining homeostasis between coagulation and fibrinolysis, expression of adhesion molecules for cells in the immune system, metabolism of noradrenaline and 5-hydroxytryptamine, and conversion of angiotensin I and bradykinin. The endothelium also regulates the underlying smooth muscle layer and vascular tone by release of endothelium-derived relaxing factors such as nitric oxide (NO), prostaglandins, and endothelium-derived hyperpolarizing factor (EDHF) as well as vasoconstricting factors such as endothelin, superoxide (O(2)), and thromboxane.

Several candidates for EDHF have been proposed, such as potassium ions, hydrogen peroxide, and epoxyeicosatrienoic acids. Prostaglandins, such as prostacyclin and prostaglandin E2 binds to specific receptors followed by increases in cyclic adenosinmonophosphate and vasorelaxation, while contractile prostaglandins constrict vessels by activation of thromboxane and endoperoxidase receptors. Superoxide anions induce contraction of vascular smooth muscles cells by scavenging NO. Endothelin is a potent endothelium-derived contractile factor. The synthesis of endothelin-1 is induced by hypoxia, thrombin, interleukin-1, transforming growth factor-beta1, vasopressin, and catecholamines.

In normal rodents, the administration of 1% arginine HCl to their normal diet (1.8% L-Arg content) increased thymic weight, secondary to increasing the numbers of total thymic T lymphocytes. This thymotropic effect was functionally correlated with enhancement of cell-mediated immunity and T-lymphocyte responses to mitogenic stimulation. In the athymic mouse, supplemental arginine increased the number of T cells and augmented delayed-type hypersensitivity responses, indicating that it can exert its effects on peripheral lymphocytes and in addition to those within the thymus. Other studies performed in both healthy human volunteers and severely ill intensive care patients indicated that the mitogenic response of peripheral blood lymphocytes is similarly increased by arginine when given at doses of 30 g/day. Following injury, arginine could reduce or abrogate the thymolytic and immunosuppressive effects of trauma and enhance rejection of allogeneic skin graft. Dietary supplementation with the semi-essential amino acid arginine enhanced T-cell-mediated immune function and stimulated wound healing and reparative collagen synthesis in healthy animals and human beings. At cellular level, arginine is metabolized by different enzymes to various end products that are involved in immunomodulation.

In addition to its importance as a structural semi-essential amino acid and its role in a variety of physiological functions, it has been postulated that L-arginine (L-Arg) is a potent modulator of macrophage functions, as these phagocytes are able to metabolize L-Arg via two major pathways: a) the arginase pathway, by which the guanidino nitrogen is incorporated into urea, with the other product being L-ornithine; and b) the nitric oxide synthase pathway, which results in oxidation of the guanidino nitrogen, in production of nitric oxide (NO) and yielding nitrite, nitrate, and citrulline as stable end products. NO is highly lipophilic and therefore rapidly traverses cell membranes, making it an effective intra- and inter-cellular messenger. It has a very short life (3-9 seconds) and must be produced in large quantities or over long periods to have prolonged biological effects. When produced by macrophages, it can rapidly enter microrganisms and tumor cells and exert cytostatic and cytotoxic effects by increasing cyclic-GMP synthesis and inhibiting host mitochondrial electron transport and DNA replication. However, macrophages also play a central role in the regulation of specific and nonspecific immunity directly or by cytokine secretion [i.e. interleukin-1 (IL-1) and tumor necrosis factor (TNF-α)] and are actually involved in immunological functions such as phagocytosis, tumoricidal and antibacterial activities. On the basis of the above concepts, one can infer that alterations in macrophage functions could have cascading effects on other immune cells.

During an inflammatory reaction, there is an increase in the number of macrophages due to the influx of bone marrow-derived monocytes at the site of the lesion and by production of macrophages in the inflammatory exudate by locally dividing cells. It was observed that sites of inflammation with prominent macrophage infiltration, such as wounds and certain tumors, are deficient in free arginine. In this regard Albina et al. (1988) reported that low concentrations of L-Arg in culture media (<0.1 mM) enhanced activation-associated functions in rat resident peritoneal macrophages, including citotoxicity against tumor cells, superoxide production, and phagocytosis. In contrast, when L-Arg is added to the culture media in concentrations ranging from the plasmatic one (about 0.1 mM) to 1.2 mM (the concentration in RPMI 1640), a suppression of superoxide production, cytotoxicity, phagocytosis and protein synthesis were observed in resident peritoneal macrophages. Moreover, the same supplemental L-Arg concentrations were able to induce an increase of cytotoxicity in Corynebacterium parvum-elicited macrophages.

In particular, a decrease in arginine availability may contribute to the activation of unprimed macrophages migrating at inflammatory sites. The reduction in free L-Arg observed in inflammatory milieu is due to the activity of macrophage-derived arginase, rather than to L-Arginine/NO pathway, since ornithine, the product of arginase activity, accumulates within extracellular space rather than citrulline, the product of L-Arg/NO pathway. These results provide evidence that the NO-pathway may not be preferentially utilized in sites of inflammation during maximal macrophage infiltrations because the remarkably low extracellular L-Arg concentrations become rate limiting for its activity.

L-Arg is one of the crucial components in the regulation of the antibacterial and antitumoral functions of macrophages under in vitro culture conditions and probably in vivo. Among several enzymes in cytotoxic macrophages, NOS and arginase seem to play the most significant role in the metabolism of L-Arg. NO, an important regulator and mediator in many physiological and pathophysiological events, is produced by the oxidation of one of the guanidino nitrogens of L-Arg by a family of NOS isoforms. Although some NOS isoforms are constitutively expressed and $Ca^{2+}$ dependent, the NOS expressed in macrophages (Mφ), known as inducible NOS (iNOS), is independent of $Ca^{2+}$ and can be induced by certain cytokines and by LPS, producing NO in the presence of a supply of L-Arg. L-Arg-dependent production of NO has been implicated in mediating the cytotoxic actions of the activated macrophages against a variety of pathogens, including yeasts, helminths, protozoa, mycobacteria and against various cellular targets, including tumor cells.

L-Arg supplementation has numerous effects on the immune system including increasing peripheral blood lymphocyte mitogenesis, increasing the T-helper to T-cytotoxic (c) cell ratio, increasing macrophage activity against microrganisms and tumor cells and decreasing the number of Tc cells. The delayed type hypersensitivity response is also increased, as is the number of circulating NK and lymphokine-activated killer cells. Therefore supplemental L-Arg is useful for patients undergoing major surgery after trauma and sepsis.

Moreover, in many pathophysiological conditions, such inflammation and sepsis, an increase of NO is evident. Since this production requires extracellular L-Arg, the manipulation of substrate availability for NOS could be an attractive target for therapeutic intervention. The combination of arginine and silicate in the arginine silicate inositol complex helps to reduce the risk of infection and reduces inflammatory markers.

It is probable that alteration of arginase activity may alter the NO production. The metabolism of L-Arg via NOS is important for macrophage anti-tumor activity and an enhancement of arginase activity could compromise this tumoricidal activity by reducing NO production. The metabolism of L-Arg to ornithine, and subsequently towards polyamines, that is induced by arginase may provoke tumor cell proliferation. L-Arg metabolism in macrophages within a tumor could either promote inhibition or growth of the tumor, depending whether the NOS or arginase pathway is prevailing.

Arginine promotes nitric oxide synthesis, which is believed to help protect against bacterial infections. Arginine can stimulate antibacterial components of the immune system. The role of nitric oxide was studied in host defense against Klebsiella pneumoniae infection of the lung. The results suggested that nitric oxide plays a critical role in antibacterial host defense against K. pneumoniae, in part by regulating macrophage phagocytic and microbicidal activity (Wang et al. J. Biomed. Sci. 6:28-35, 1999).

Silica supplementation helps repair and maintain vital lung tissues and protects them from pollution. It acts as a cough decreasing agent. Silica tones the upper respiratory tract (nose, pharynx, larynx), reduces swelling due to its positive actin on the lymphatic system, reduces stress during menopause, works with other antioxidants to prevent premature aging, can help prevent kidney stones and can promote healing infection of the urinary tract. It is a natural diuretic which can increase excretion of urine by 30 percent. The presence of sufficient silica in the intestines will reduce inflammation of the intestinal tract. It can cause disinfection in the case of stomach and intestinal catarrh and ulcers. Silica can prevent or treat both diarrhea and constipation and can help normalize hemorrhoidal tissues and bowel function. Silica can alleviate lower bank pain and has been effective for treating female discharge, abscesses and ulcers in the genital area and cervix, as well as mastitis. Silica acts as a supportive treatment for the inflammation of the middle ear. Other qualities of silica supplementation can include stimulating the immune system, normalizing circulation, regulating high blood pressure and decreasing vertigo, headache, tinnitus (buzzing of the ears) and insomnia. Silica can help treat diabetes by promoting synthesis of elastase inhibitor by the pancreas, can help arterial disease by strengthening the blood vessels and can help prevent tuberculosis. It also improves the elasticity of the joints, and can help treat rheumatism.

In another preferred embodiment, an arginine silicate inositol complex is administered to an individual at risk for a bone or cartilage disorder. The disorder may be osteoporosis, osteogenesis imperfecta, bone fractures, osteoarthritis, inflammatory arthritis, a torn tendon or a torn ligament. By administering an arginine silicate inositol complex to an at risk individual, bone tissue can be strengthened preemptively and the symptoms of the disorder can be avoided.

In another preferred embodiment, the administration of an arginine silicate inositol complex maintains or increases the levels of collagen type I in an individual. Collagen type I comprises 95% of the extracellular non-mineral bone matrix and synthesis of this protein by osteoblasts is an important step in the formation of bone material. By maintaining levels of collagen type I, loss of bone material in an individual at risk for such loss may be reduced.

In another preferred embodiment, an arginine silicate inositol complex is administered to an individual, preferably a mammal, in order to stimulate an increase in bone weight or in femur length.

In another preferred embodiment, an arginine silicate inositol compound is administered to an individual to prevent or treat bone loss due to a reduction in mechanical stress on the body, specifically on the skeletal system. Reduction of mechanical stress can lead to a loss of bone mass in an individual by altering the homeostatic balance between osteoblasts, which promote bone formation, and osteoclasts, which promote bone resorption and a weakening of the bone matrix. Mechanical stress can be reduced by immobilization, such as when a limb in placed in a cast in order to heal a fracture, or during weightless conditions that occur during space flight. By administering an arginine silicate inositol compound, bone formation can be stimulated and the bone-wasting effects of reduced mechanical stress can be avoided or treated.

As described above, arginine plays a crucial role in the generation of nitric oxide by the vascular endothelium, which produces NO through the oxidation of arginine by nitric oxide synthases (NOS). NO produced by the vascular endothelium has a vasoprotective, anti-inflammatory and anti-oxidative effect. Research has linked vascular endothelium NO production or its regulation to a variety of diseases and disorders, including renal diseases, pulmonary hypertension, systemic sclerosis of the cardiovascular system, chronic heart failure, chronic obstructive pulmonary disease (COPD), hypertension, diabetes, chronic hyperglycemia, inflammation and hypercholesterolemia. For example, in both diabetic patients and healthy individuals, inhibition of NO synthesis lead to decreased glucose uptake during exercise.

Another preferred embodiment of the invention includes the use of an arginine silicate inositol complex in the treatment or prevention of insulin resistance and improving the response to insulin in patients.

In another embodiment, an arginine silicate inositol complex is administered to patients to treat, alleviate the symptoms of or prevent the occurrence of disease states and disorders linked to insulin resistance.

Another aspect of the invention relates to a method of inhibiting the development of a secondary disease resulting from insulin resistance. In a preferred embodiment of this aspect of the invention, an arginine silicate inositol complex is given to a patient being treated with a medication that induces or puts the patient at risk for insulin resistance.

Numerous drug therapies have been implicated in causing drug-induced insulin resistance. For example, the use of statins, non-steroidal anti-inflammatory drugs (NSAIDS), steroids, oral contraceptives, hormone replacement therapy (HRT), beta blockers, potassium channel openers, and diuretics have been linked to an increased incidence of insulin resistance.

As used herein, the phrase "drug which induces insulin resistance" means any substance which may induce insulin resistance when administered to a human or other animal. Examples of drugs which induce insulin resistance include, without limitation, statin drugs such as simvastatin, cerivastatin, pravastatin, atorvastatin, fluvastatin, and lovastatin; non-steroidal anti-inflammatory drugs such as cimicifuga, choline salicylate-magnesium salicylate, diclofenac sodium, diclofenac potassium, diflunisal, etodolac, fenoprofen calcium, floctafenine, flurbiprofen, ibuprofen, indomethacin, ketoprofen, ketorolac tromethamine, magnesium salicylate, mefenamic acid, nabumetone, naproxen, naproxen sodium, oxyphenbutazone, phenylbutazone, piroxicam, salsalate, sodium salicylate, sulindac, tenoxicam, taiprofenic acid, and tolmetin sodium; steroids such as hydrocortisone, dexamethasone, and methylprednisolone; contraceptives including oral contraceptives such as estrogen, progesterone and progestin as well as implantable contraceptives such as levonorgestrel, etonogestrel, nomegestrol acetate, and nestorone; hormone replacement therapy (HRT) drugs including conjugated equine estrogens, esterified estrogens, estradiol, estrone, synthetic conjugated estrogens, estropipate, estropipate, ethinyl estradiol, norethindrone, medroxyprogesterone acetate, progestin, natural progesterone, tamoxifen, testosterone, and raloxifene; beta blocker drugs including acebutolol, atenolol, betaxolol, bucinodol, carteolol, labetalol, metoprolol, nadolol, penbutolol, pindolol, propanolol, and timolol; and diuretics. Three primary types of diuretics exist which include thiazides, loop diuretics, and potassium sparing agents. As used herein, the term "diuretic" or "diuretics" includes, without limitation, hydrochlorothiazide, chlorthalidone, chlorothiazide, indapamide, metolazone, amiloride, spironolactone, triamterene, furosemide, bumetanide, ethacrynic acid, and torsemide. Certain immunosuppressive drugs such as prednisolone, cyclosporin A, and tacromlimus and potassium channel modulators such as nicorandil are also included in the definition of drugs which induce insulin resistance. The above list is provided for example purposes only and it is understood that the definition of "drug which induces insulin resistance" includes those drugs which induce insulin resistance that are not specifically listed above, as well as those drugs which are found to induce insulin resistance, whether in existence today or developed in the future.

The administration of an effective dose of an arginine silicate inositol complex to subjects who are taking drugs which have been linked with the onset of insulin resistance actually inhibits or attenuates the onset of insulin resistance. The supplementation with an arginine silicate complex to a subject taking a drug which induces insulin resistance results in a lowered incidence of drug-induced insulin resistance. By not developing insulin resistance in the first place, the patient is not exposed to the associated diseases and risks. The patient also does not need to take additional, and sometimes costly, medications to treat the insulin resistance and associated diseases.

Without being limited to a particular theory, we propose that supplementation with an arginine silicate inositol complex inhibits drug-induced insulin resistance from developing by reducing fasting insulin levels and lowering blood sugar. Accordingly, in one embodiment, a method of inhibiting drug-induced insulin resistance through supplementation with an arginine silicate inositol complex is provided.

The amount of an arginine silicate inositol complex necessary to obtain the desired effect, i.e., to thwart the development of insulin resistance, will depend on the particular insulin-resistance-inducing-drug and dosage of such drug that the subject is required to take. In general, the amount of an arginine silicate inositol complex used for supplementation in order to inhibit the onset of drug-induced insulin resistance is at least about 50 μg/day. Preferably, the amount of the arginine silicate inositol complex is between about 50 μg/day and 7,500 mg/day. More preferably, the arginine silicate inositol is administered three times daily in an amount ranging from about 250 mg to about 2,500 mg. In a particularly preferred embodiment, the compounds are administered three times daily in an amount ranging from about 500 mg to about 1,000 mg. It is also contemplated that the compounds may be administered once or twice a day rather than three times, depending on the severity of the symptoms being treated. Note that these doses are based on a 70 kg adult human, and that the dose can be applied on a per-kilogram basis to humans or animals of different weights.

Inhibition of drug-induced insulin resistance is accomplished by administering a drug which induces insulin resistance and an effective dose of an arginine silicate inositol complex to an individual separately or as a single composition. A subject may begin arginine silicate inositol supplementation at the beginning of their treatment with insulin-resistance-inducing-drugs. Alternatively, the subject may begin supplementation with an arginine silicate inositol complex after the subject's treatment with insulin-resistance-inducing-drugs has begun, but before developing insulin resistance.

Insulin resistance is a key pathogenic parameter of Type 2 diabetes, and clinical interventions that improve insulin sensitivity are considered cornerstones in the management of the disease. In addition, the relationship of insulin resistance to cardiovascular disease and its associated risk factors has been well established over the past few years. Therefore, in a preferred embodiment, methods and compositions for thwarting the development of insulin resistance are provided comprising the administration of an arginine silicate inositol complex and a hypoglycemic drug such as metformin inhibit insulin resistance from developing. Combinations of pharmacologic agents (such as sulfonylureas/metformin, sulfonylureas/glitazones, and metformin/glitazones) are highly effective pharmacologic interventions that appear to lower both glucose and insulin levels. Further, there is evidence that triple drug therapy (e.g. sulfonylureas/metformin/glitazones) can lower clinical glycemia in addition to lowering insulin levels. Hence, in some embodiments, compositions comprising an arginine silicate inositol complex with metformin, sulfonylureas, and glitazones or combinations thereof are administered to a subject taking drugs which are induce insulin resistance to inhibit the onset of such insulin resistance.

In another preferred embodiment, an arginine silicate inositol complex is used to improve the coronary vascular health of an individual. Additionally, such a complex can be used to prevent diseases or disorders through the improvement of coronary vascular health, such as sclerosis of the kidney, abnormal liver lipid metabolism and complications of the vascular system on both a small and a large scale.

An arginine silicate inositol complex can also be used to reduce markers of poor cardiovascular health and increase markers of good cardiovascular health. For example, an arginine silicate inositol complex is administered to a patient with elevated urinary albumin concentrations or in whom tests have indicated an increased level of vascular contractility, in order to reduce these markers of poor cardiovascular health. In another example, an arginine silicate inositol complex is administered to a patient in order to improve a marker of good cardiovascular health, such as vascular relaxation.

The compounds of the invention may be administered parenterally, orally, intravenously, intraarterially, intramuscularly or in any other systemic fashion, in appropriate dosage units, as desired. The term "parenteral" used herein includes subcutaneous, intravenous, intraarterial, injection or infusion techniques, without limitation. However, oral administration is preferred. The compounds of the invention may be in a powder form, liquid form or a combination of powder and liquid forms. For oral administration, the compounds may be provided as a tablet, aqueous or oral suspension, dispersible powder or granule, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents, preservatives, solubilizers, wetting agents, stabilizers, colorants, antioxidants, coating agents and diluents. The sweetening agents and flavoring agents will increase the palatability of the preparation. Tablets containing arginine silicate inositol in admixture with non-toxic pharmaceutically acceptable excipients suitable for tablet manufacture are acceptable. Such excipients include inert diluents such as calcium carbonate, sodium carbonate, lactose, calcium phosphate or sodium phosphate; granulating and disintegrating agents such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the compounds of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent and one or more preservatives. Additional excipients, for example sweetening, flavoring and coloring agents, may also be present. Syrups and elixirs may be formulated with sweetening agents such as glycerol, sorbitol or sucrose. Such formulations may also include a demulcent, a preservative, a flavoring or a coloring agent. For assistance in formulating the compositions of the present invention, one may refer to Remington's Pharmaceutical Sciences, 15th Edition, Mack Publishing Co., Easton, Pa.

The arginine silicate inositol preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono- or diglycerides. In addition, fatty acids such as oleic acid may likewise be used in the to prepare injectable preparations.

The disclosed compounds can also be administered by inhalation. In this administration route, an arginine silicate inositol complex can be dissolved in water or some other pharmaceutically acceptable carrier liquid for inhalation, or provided as a dry powder, and then introduced into a gas or powder that is then inhaled by the patient in an appropriate volume so as to provide that patient with a measured amount of an arginine silicate inositol complex. Examples of the administration of a therapeutic composition via inhalation are described in U.S. Pat. Nos. 6,418,926; 6,387,394; 6,298,847; 6,182,655; 6,132,394; and 6,123,936, which are hereby incorporated by reference.

Infusion devices can be used to deliver the disclosed compounds. Suitable devices include syringe pumps, auto injector systems and minipumps. Exemplary devices include the Ambulatory Infusion Pump Drive, Model 30, available from Microject Corp., Salt Lake City, Utah, and the Baxa Syringe Infuser, available from Baxa Corporation, Englewood, Colo. Any device capable of delivering the disclosed compounds in accordance with the methods disclosed herein can be used.

Suitable infusion devices preferably have an effective amount of an arginine silicate inositol complex contained therein. The device can be pre-loaded with the desired substance during manufacture, or the device can be filled with the substance just prior to use. Pre-filled infusion pumps and syringe pumps are well known to those of skill in the art. The active substance can be part of a formulation which includes a controlled release carrier, if desired. A controller is used with the device to control the rate of administration and the amount of substance to be administered. The controller can be integral with the device or it can be a separate entity. It can be pre-set during manufacture, or set by the user just prior to use. Such controllers and their use with infusion devices are well known to those of skill in the art.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodable polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released are also well known and can be used in the disclosed methods.

In one embodiment, the disclosed compounds are administered through a topical delivery system. The controlled release components described above can be used as the means to delivery the disclosed compounds. A suitable topical delivery system comprises the disclosed compounds in concentrations taught herein, a solvent, an emulsifier, a pharmaceutically acceptable carrier material, penetration enhancing compounds, and preservatives. Examples of topically applied compositions include U.S. Pat. Nos. 5,716,610 and 5,804,203, which are hereby incorporated by reference. The compositions can further include components adapted to improve the stability or effectiveness of the applied formulation, such as preservatives, antioxidants, skin penetration enhancers and sustained release materials. Examples of such components are described in the following reference works hereby incorporated by reference: *Martindale—The Extra Pharmacopoeia* (Pharmaceutical Press, London 1993) and Martin (*ed.*), *Remington's Pharmaceutical Sciences*.

Controlled release preparations can be achieved by the use of polymers to form complexes with or absorb the arginine silicate inositol complex. The controlled delivery can be exercised by selecting appropriate macromolecule such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active compound.

Controlled release of active compounds within the scope of this invention can be taken to mean any of the extended release dosage forms. The following terms may be considered to be substantially equivalent to controlled release, for the purposes of the present invention: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein an arginine silicate inositol complex is dissolved in an aqueous constituent to gradually release over time, can be prepared by copolymerization of hydrophilic mono-olefinic monomers such as ethylene glycol methacrylate. Matrix devices, wherein an arginine silicate inositol complex is dispersed in a matrix of carrier material, can be used. The carrier can be porous, non-porous, solid, semi-solid, permeable or impermeable. Alternatively, a device comprising a central reservoir of an arginine silicate inositol complex surrounded by a rate controlling membrane can be used to control the release of the complex. Rate controlling membranes include ethylene-vinyl acetate copolymer or butylene terephthalate/polytetramethylene ether terephthalate. Use of silicon rubber depots are also contemplated.

Controlled release oral formulations are also well known. In one embodiment, the active compound is incorporated into a soluble or erodible matrix, such as a pill or a lozenge. Such formulations are well known in the art. An example of a lozenge used to administer pharmaceutically active compounds is U.S. Pat. No. 5,662,920, which is hereby incorporated by reference. In another example, the oral formulations can be a liquid used for sublingual administration. An example of pharmaceutical compositions for liquid sublingual administration of the disclosed compounds are taught in U.S. Pat. No. 5,284,657, which is hereby incorporated by reference. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process. In a preferred embodiment, transdermal patches, steady state reservoirs sandwiched between an impervious backing and a membrane face, and transdermal formulations, can also be used to deliver an arginine silicate inositol complex. Transdermal administration systems are well known in the art. Occlusive transdermal patches for the administration of an active agent to the skin or mucosa are described in U.S. Pat. Nos. 4,573,996, 4,597,961 and 4,839,174, which are hereby incorporated by reference. One type of transdermal patch is a polymer matrix in which the active agent is dissolved in a polymer matrix through which the active ingredient diffuses to the skin. Such transdermal patches are disclosed in U.S. Pat. Nos. 4,839,174, 4,908,213 and 4,943,435, which are hereby incorporated by reference.

Steady state reservoirs for use with the disclosed compounds delivery a suitable dose of those compounds over a predetermined period of time. Compositions and methods of manufacturing compositions capable of absorption through the mucosal tissues are taught in U.S. Pat. No. 5,288,497, which is hereby incorporated by reference. One of skill in the art could readily include the disclosed compounds and related compositions.

Another method to control the release of an arginine silica complex is to incorporate the complex into particles of a polymeric material such as polyesters, polyamino acids, hydrogels, poly lactic acid, or ethylene vinylacetate copolymers.

Alternatively, instead of incorporating an arginine silicate inositol complex into these polymeric particles, the complex is entrapped in microcapsules prepared, for example, by coacervation techniques, or by interfacial polymerization, for example hydroxymethylcellulose or gelatin-microcapsules, respectively, or in colloidal drug delivery systems, for example, liposomes, albumin microspheres, microemulsions, nanoparticles, and nanocapsules, or in macroemulsions. Such technology is well known to those of ordinary skill in pharmaceutical sciences.

Optionally, the pharmaceutical compositions of the invention may comprise the arginine silicate inositol complex combined with one or more compounds exhibiting a different activity, for example, a calcium supplement, an anti-diabetic drug such as metformin, or other pharmacologically active material.

The amount of arginine silicate inositol that may be combined with the carrier material to produce a single dosage form will vary depending upon the host treated and the particular form of administration.

In a preferred embodiment, as a preventative or therapeutic agent for bone and cartilage disorders, cardiovascular disorders or disorders related to metabolic syndrome, arginine silicate inositol is administered three times daily in an amount ranging from about 2 mg to about 2,500 mg. In a particularly preferred embodiment, the compounds are adminstered three times daily in an amount ranging from about 500 mg to about 1,000 mg. Note that these doses are based on a 70 kg adult human, and that the dose can be applied on a per-kilogram basis to humans or animals of different weights. For example, in another embodiment, arginine silicate inositol is administered three times daily in an amount ranging from about 2 mg/kg of body weight to 2,500 mg/kg of body weight. It is also contemplated that the compounds may be administered once or twice a day, rather than three times, depending on the severity of the symptoms being treated.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

The synthesis and use of arginine silicate inositol compounds are described in the following examples.

EXAMPLE 1

Preparation of Arginine Silicate Inositol

Arginine (3.8 g, 21.8 mmol) was added to a vigorously stirred solution of inositol (1.25 g, 6.9 mmol) in potassium silicate [5 ml, 29.8° Be, 8.3% $K_2O$ (0.52 g, 5.5 mmol), 20.8% $SiO_2$ (1.3 g, 21.8 mmol)], resulting in a highly viscous suspension. The suspension was heated to 95° C. Heating and stirring were discontinued when the mixture became clear and started to form a gel. The mixture was left overnight at room temperature and allowed to crystallize. The resulting crystal bulk was dispersed, mixed with ethanol (5 ml) and left for 30 minutes. This procedure was repeated with another 5 ml ethanol on the resulting crystals and left overnight to complete crystallization. The final arginine silicate inositol product was collected by filtration, washed with ethanol and dried under vacuum. The amount of product was 7.7 g obtained as a hydrate (111% of the total mass of the used reagents.

An analytical sample kept under vacuum at 90° C. for 1 hour lost 11.5% of its mass due to removal of water. Elemental analysis indicated: 25.13% C, 6.24% H, 14.11% N, 8.25% Si (17.68% $SiO_2$). The potassium content (5.4%) was determined using a kit (HACH Co., Loveland Colo., Catalog No. 234394) based on the well-known tetraphenylborate method. These results are in agreement with the calculated content of elements in the arginine silicate inositol product.

EXAMPLE 2

Kinetics of Arginine Silicate Inositol Product

Studies of the kinetics in aqueous solution of the arginine silicate product indicated the formation of non-dissociable arginine silicate complex as a function of used concentration. Measurement of the ratio of dissociated to non-dissociated forms of arginine silicate was performed using a HACH kit (Catalog No. 24296-00) in which the absorbance at 452 nm is a function of the concentration of silicomolybdate formed under acid conditions and expressed as % of silica ($SiO_2$). An aqueous solution of arginine silicate product (10 g/l) was diluted at the appropriate time to 0.5 g/L and the content of silica was measured using the HACH method. The level of silica at time 0 was 17.5%; at 1 hour was 11.8%; at 2 hours was 10.8%; and at 24 hours was 9.2%. In an aqueous solution of 0.5 g/l arginine silicate, the level of silica was 17.5% and was stable after 24 hours, confirming the solubility of the product.

EXAMPLE 3

Bioavailability of Arginine Silicate Inositol

A solution (8 g/l) of arginine silicate was prepared and, after donating a baseline 24-hour urine, a human volunteer consumed three one-cup servings daily for three days. On the third day, he once again obtained a 24-hour urine. Silicon assay revealed that urinary silicon output has increased more than tenfold from baseline. The amount of silicon in the third-day urine corresponded to approximately 25% of the silicon-ingested daily from the arginine silicate solution. This demonstrated improved bioavailability of the silicon in solubilized arginine silicate.

EXAMPLE 4

Effects of Arginine Silicate Inositol Complex on Metabolism and Vascular Function in an Insulin-Resistant Rat Model This study examines the effects of dietary supplementation with arginine silicate inositol on the health of the JCR:LA-cp strain of rat. The JCR:LA-cp rat is known to spontaneously develop the range of dysfunction and pathophysiology associated with Metabolic Syndrome in humans, e.g., obesity, profound insulin resistance, atherosclerosis with enhanced vascular contractility, and reduced vascular relaxation. In addition, obese male rats spontaneously develop ischemic lesions of the heart and are prone to stress-induced myocardial infarcts that can be fatal. Insulin resistance develops rapidly in young rats between the ages of 4 and 7 weeks and is highly correlated with the cardiovascular disease. Male rats have markedly increased urinary albumin excretion at 12 weeks of age, when insulin levels are very high, but not at 39 weeks of age, when insulin levels have dropped from the peak seen at 26 weeks. Consistent with this observation is the presence of glomerular sclerosis in the older rats.

Male JCR: LA-cp rats are maintained on a reversed light cycle at 3 or 7 weeks of age and acclimatized over a 1-week period. This allows metabolic studies to be conducted under subdued light, during the active (dark) phase of their diurnal cycle.

Rats are treated with arginine silicate inositol supplemented feed from 4 or 8 weeks of age, before insulin resistance has developed and after insulin resistance syndrome is fully established, to 13 weeks of age. Arginine silicate inositol is incorporated into a commercially available feed (Lab Diet 5001 from PMI International) at concentrations of 500 mg arginine as arginine silicate per kilogram of feed, 3 g arginine as arginine silicate per kilogram of feed, and 9 g arginine as arginine silicate per kilogram of feed. The rats are divided into four groups and receive one of the three aforementioned feed concentrations or unsupplemented feed. The dosage is maintained on either a mg/kg body weight basis, in which case the diet is formulated on a weekly basis to ensure each rat receives the intended dose on a mg/kg basis, or the specified concentration in the feed. Food consumption and body weights are measured twice weekly.

At 12 weeks of age, rats fast over the light (non-active) phase. A fasting blood sample is obtained from the tail and a standardized meal tolerance test (MTT) is performed. Following a 2-day recovery period, the rats are placed in a metabolism cage for 24 hours for the collection of urine.

At 13 weeks of age, rats in the fed state are sacrificed under anesthesia with halothane in oxygen, and the following tissues are removed for processing as described below:
1. Thoracic aorta for vascular function studies;
2. Heart; cut transversely and snap frozen, base for fatty acid assays and apex for molecular biology;
3. Kidney, liver and pancreas for histology;
4. Liver snap frozen, samples for molecular biology and biochemical assay;
5. One soleus muscle snap frozen for gene and protein expression and the contralateral for lipid assay;
6. One epitrochlearis brachii muscle fixed in glutaraldehyde for possible TEM visualization of intracellular lipid;
7. Perirenal fat pad, snap frozen in two samples; and
8. Blood for separation of serum and plasma.

The following parameters are measured: Food intake and body weights, glucose and insulin response (through a meal tolerance test), plasma total lipid profile, ratio of urine albumin to creatinine, plasma levels of leptin, C-reactive protein and tumor necrosis factor alpha (TNFα), vascular function studies on aortic rings (contractility/relaxation), modulation of levels and activity of peroxisome proliferator-activated receptors (PPARs), fatty acid composition of plasma cholesterol esters, liver, pancreas, muscle and adipose tissue, and phosphatidylinositol-3 (PI-3) Kinase Signaling. Histological analysis are obtained for: glomerular sclerosis; islet morphometry; liver-hepatic damage and lipid content; and muscle (potential electron microscopy for lipid). Tables 1, 2 and 3 show data for vascular contractility, reactive hyperemia & bradykinin response and relaxant response, respectively.

TABLE 1

Logistic Curve Fit Parameters for Contractile Response of Aortic Rings to Phenylephrine in Male JCR: LA-cp Rats

|  | $EC_{50}$ ($M \times 10^{-6}$) | P | Maximum contraction (g) | P | Slope | P |
|---|---|---|---|---|---|---|
| +/? control | 7.63 <≡ ~1.10 |  | 1.45 <≡ ~0.06 | $<10^{-4}$ | −1.19 <≡ ~0.22 |  |
| cp/cp control | 6.87 <≡ ~1.69 | NA | 1.94 <≡ ~0.10 | NA | −0.788 <≡ ~0.117 | NA |
| cp/cp arginine silicate-treated | 8.58 <≡ ~1.05 |  | 1.44 <≡ ~0.07 | $<10^{-4}$ | −1.01 <≡ ~0.17 |  |
| cp/cp arginine HCl-treated | 7.13 <≡ ~1.12 |  | 1.84 <≡ ~0.07 |  | −1.03 <≡ ~0.14 |  |

Values are mmol/l; mean <≡~ SEM, 8-9 rats in each group. The program ALLFIT was used to obtain logistic curve parameters and the significance of differences between groups.
P values are compared to those of cp/cp control animals.
NA, not applicable.

TABLE 2

Parameters for Hearts of Male JCR: LA-cp Rats

|  | Coronary flow (ml/min) | Reactive hyperemia (%) | Bradykinin response | |
|---|---|---|---|---|
|  |  |  | Maximum response relative flow | log $EC_{50}$ |
| +/? control | 10.9 ± 0.5 | 183 ± 15** | 1.98 ± 0.94 | −5.32 ± 0.90 |
| cp/cp control | 11.5 ± 0.40 | 122 ± 0.6 | 1.19 ± 0.05 | −4.9 ± 3.37 |
| cp/cp arginine silicate-treated | 10.8 ± 0.4 | 186 ± 25.3* | 1.95 ± 0.40 | −5.64 ± 1.19 |
| cp/cp arginine HCl-treated | 10.5 ± 0.3 | 170 ± 11** | 1.48 ± 0.55 | −6.19 ± 4.00 |

Values are mean ± SEM, 10 rats in each group.
*p < 0.05,
**p < 0.01 vs cp/cp control.
The bradykinin response of coronary flow of the arginine silicate-treated group was significantly different from that of the cp/cp control group in overall parameter values (p = 0.001).

TABLE 3

Logistic Curve Fit Parameters of Relaxant Response of Aortic Rings to Acetylcholine

| Group | $EC_{50}$ M × $10^{-6}$ | P | Maximum Relaxation % | P | Slope | P |
|---|---|---|---|---|---|---|
| +/? | 1.43 ± 0.39 | 0.032* | 92.6 ± 4.7 | * | −0.620 ± 0.096 | * |
| cp/cp control | 3.27 ± 0.80 | NA | 88.2 ± 4.3 | NA | −0.806 ± 0.129 | NA |
| cp/cp arginine-silicate | 2.05 ± 0.45 | * | 97.1 ± 4.0 | * | −0.729 ± 0.105 | * |
| cp/cp arginine HCl | 1.25 ± 0.27 | 0.002* | 90.4 ± 3.5 | * | −0.673 ± 0.093 | * |

Aortic rings were pre-contracted with phenylephrine to 80% of maximal response.
*significantly different from cp/cp if all three coefficients considered together (p < 0.001).

Rats supplemented with dietary arginine silica complex show reduced metabolic syndrome and cardiovascular disease (CVD) symptoms as compared to controls. For rats that began treatment at 4 weeks of age, before the onset of metabolic syndrome and CVD symptoms, the increases in urinary albumin excretion and serum insulin concentration at 12 weeks are reduced as compared to the very large increases in the control group. The animals from the experimental group, as compared to control animals, show greater sensitivity to insulin, greater tolerance to glucose, reduction in body weight, insulin resistance, coronary risk lipids and lipoprotein concentrations, decreased vascular contractility and glomerular sclerosis, increased vascular relaxation, reduced ischemic lesions and stress induced myocardial infarct, lower levels of islet cell hyperplasia, reduced structural remodeling (e.g., enlargement of the heart and other visibly-apparent vascular abnormalities), as well as improved endothelial function, decreased levels of inflammatory markers, enhanced gene expression and PPAR (α,γ) activity, and enhanced insulin signaling pathway. FIG. 1 shows the changes in coronary blood flow and improved bradykinin response.

EXAMPLE 5

Use of an Arginine Silicate Inositol Complex to Improve Markers of Bone Turnover and Reduce Risk of a Bone Disorder A subject at risk for bone loss due to age, menopause, andropause, immoblization or another cause has shown elevated levels of the N-telopeptide of collagen type I and reduced levels of osteocalcin in tests of the subject's blood serum as compared to the normal range of concentration for those markers. The subject is placed on a daily regime of an arginine silicate inositol complex, 500 mg total per day. After several weeks have elapsed, the blood tests are repeated and show that the concentrations of those markers of bone resorption and formation have returned to their normal ranges. After several months on the regime have elapsed, a measurement of bone mineral density shows an optimal level of bone density for an individual of the subject's age, a level of density that correlates with a below average risk for bone fractures or other adverse events.

EXAMPLE 6

Use of an Arginine Silicate Inositol Complex to Treat Symptoms of Metabolic Syndrome An overweight subject undergoes testing that reveals abnormal glucose metabolism and concentrations of cholesterol and triglycerides in blood serum that are above the normal range for one of the subject's age group. The subject is placed on a daily regime of an arginine silicate inositol complex, 500 mg total per day. After several weeks have elapsed, the blood tests are repeated and show that glucose metabolism has normalized and that the blood lipid concentrations that were initially higher than normal are reduced.

While particular embodiments of the invention have been described in detail, it will be apparent to those skilled in the art that these embodiments are exemplary rather than limiting, and the true scope of the invention is that defined by the appended claims.

EXAMPLE 7

Drug Formulation Including an Arginine Silicate Inositol Complex to Inhibit the Onset of Drug-Induced Insulin Resistance and CVD Risk Oral contraceptives and psychiatric drugs have long been associated with glucose resistance and/or CVD risk. Women who take oral contraceptives have an increased risk of developing drug-induced insulin resistance and are at higher risk for CVD. Accordingly, it would be of great benefit to human health to develop formulations of oral contraceptives and psychiatric drugs with an arginine silicate inositol complex to thwart the development of drug-induced CVD risk and the attendant diseases associated with CVD such as arterial thrombosis, stroke, diabetes, and hypercholesterolemia.

An effective pharmacological amount of an oral contraceptive is formulated in combination with an arginine silicate inositol complex as a tablet. The tablet contains 5-mg/kg body weight of the arginine silicate inositol complex. The oral contraceptive containing arginine silicate inositol has a lower incidence of causing drug-induced insulin resistance and higher CVD risk than those oral contraceptives which lack an arginine silicate inositol complex.

What is claimed is:

1. A method of decreasing insulin resistance in an individual, comprising;
   identifying an individual in need of decreased insulin resistance; and
   administering to said individual an effective amount of an arginine silicate inositol complex.

2. The method of claim 1, wherein said administering step is parenteral or oral.

3. The method of claim 1, wherein said effective amount of said arginine silicate inositol complex is between about 2 mg/kg body weight and about 2,500 mg/kg body weight.

4. The method of claim 3, wherein said effective amount of said arginine silicate complex is between about 5 mg/kg body weight and about 1,000 mg/kg body weight.

5. The method of claim 1, wherein said individual is a mammal.

6. A method for increasing nitric oxide production in an individual, comprising the step of administering to said individual an effective amount of an arginine silicate inositol complex.

7. The method of claim 6, wherein said administering step is parenteral or oral.

8. The method of claim 6, wherein said effective amount of said arginine silicate complex is between about 2 mg/kg body weight and about 2,500 mg/kg body weight.

9. The method of claim 7, wherein said individual is a mammal.

10. A method for treating a disorder caused by or exacerbated by reduced levels of nitric oxide by increasing concentrations of nitric oxide in an individual, comprising;
    identifying an individual in need of an increased concentration of nitric oxide; and
    administering to said individual an effective amount of an arginine silicate inositol complex.

11. The method of claim 10, wherein said disorder is selected from the group consisting of pulmonary hypertension, renal disease, hypertension, diabetes, hypercholesterolemia, hyperglycemia, heart failure, Fabry's disease, chronic obstructive pulmonary disease (COPD), inflammatory bowel disease, Crohn's disease, ulcerative colitis, perinatal asphyxia, meconium aspiration syndrome, Group B strep sepsis, congenital diaphragmatic hernia, isehemic heart disease, hyperhomocysteinemia, multiple sclerosis, Takayasu's arteritis, autosomal dominant polycystie kidney disease, end-stage renal failure, and liver disease.

12. The method of claim 10, wherein said arginine silicate inositol complex is administered parenterally or orally.

13. The method of claim 10, further comprising administering a second beneficial agent effective in treating a disorder caused by or exacerbated by reduced levels of NO, wherein said second beneficial agent is a conventional therapy for NO deficiencies.

14. The method of claim 10, wherein said effective amount of arginine silicate complex is between about 2 mg/kg body weight and about 2,500 mg/kg body weight.

15. The method of claim 10, wherein said individual is a mammal.

* * * * *

UNITED STATES PATENT AND TRADEMARK OFFICE
CERTIFICATE OF CORRECTION

PATENT NO. : 7,576,132 B2
APPLICATION NO. : 11/146620
DATED : August 18, 2009
INVENTOR(S) : Juturu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1108 days.

Signed and Sealed this

Seventh Day of September, 2010

David J. Kappos
*Director of the United States Patent and Trademark Office*